United States Patent [19]

Laval et al.

[11] Patent Number: 4,970,311
[45] Date of Patent: Nov. 13, 1990

[54] 4,6-DI-(3-AMINO-5-NITRO-1,2,4-TRIAZOLE)-5-NITROPYRIMIDINE

[75] Inventors: Francois Laval; Christian Wartenberg, both of Monts; Marie Louise Morignat, Tours, all of France

[73] Assignee: Commissariat A L'Energie Atomique, Paris, France

[21] Appl. No.: 280,576

[22] Filed: Dec. 6, 1988

[30] Foreign Application Priority Data

Dec. 8, 1987 [FR] France .................. 87 17059

[51] Int. Cl.$^5$ ........................................... C07D 413/14
[52] U.S. Cl. .................................................. 544/328
[58] Field of Search ......................................... 544/328

[56] References Cited

U.S. PATENT DOCUMENTS 2,987,520  6/1961  Sickman ..................... 260/308
3,483,211 12/1969  Coburn ....................... 260/308
3,923,804 12/1975  Sitzmann et al. .......... 260/251 R Primary Examiner—John M. Ford
Attorney, Agent, or Firm—Pearne, Gordon, McCoy & Granger

[57] ABSTRACT

The invention relates to a novel pyrimidine derivative, which is 4,6-di-(3-amino-5-nitro-1,2,4-triazole)-5-nitropyrimidine of formula:

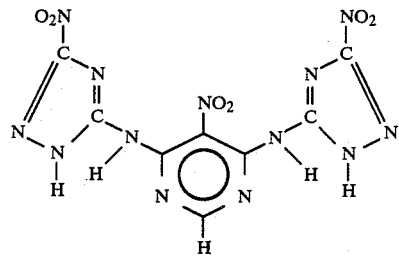

It can be prepared by reacting a dihalogeno nitropyrimidine with an alkali metal salt of 3-amino-5-nitro-1,2,4-triazole. It can be used as a secondary explosive.

1 Claim, No Drawings

4,6-DI-(3-AMINO-5-NITRO-1,2,4-TRIAZOLE)-5-NITROPYRIMIDINE

DESCRIPTION

The present invention relates to a novel pyrimidine derivative, its preparation process and its use as an explosive. More specifically, it relates to a novel pyrimidine derivative usable as a secondary explosive for equipping missiles and modern armaments.

For these applications, it is often of interest to use explosives having a minimum shock sensitivity, but a high power, i.e. a capacity to deliver a very high energy. It is very difficult to find these two properties simultaneously in the same explosive. Thus, triaminotrinitrobenzene (TATB) is very insensitive to shock, but lacks power, whereas cyclotetramethylene tetranitramine (octogen) is very powerful, but more sensitive to shock and to attacks.

It is for this reason that research is being carried out in order to develop novel explosives having a shock sensitivity close to that of TATB, whilst still being able to deliver a higher energy than the latter and similar to that of octogen.

The present invention specifically relates to a novel pyrimidine derivative having such properties.

The novel pyrimidine derivative according to the invention is 4,6-di-(3-amino-5-nitro-1,2,4-triazole)-5-nitropyrimidine in accordance with the formula:

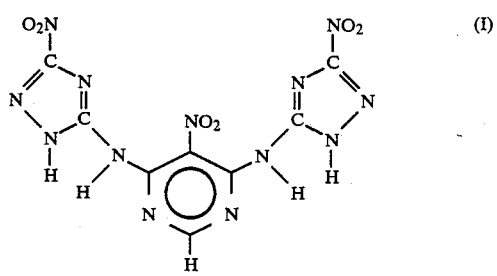

This novel pyrimidine derivative is of great interest for use as a secondary explosive, because its detonation properties are intermediate between those of TATB and those of octogen with regards to the shock sensitivity and the detonation velocity.

This novel pyrimidine derivative can be prepared by a process consisting of reacting a 4,6-dihalogeno-5-nitropyrimidine of formula:

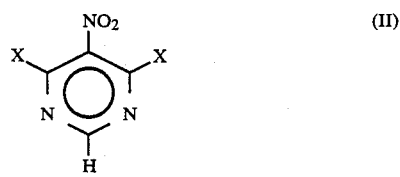

in which X represents a fluorine, chlorine or bromine atom with 3-amino-5-nitro-1,2,4-triazole or its alkali metal salt of formula:

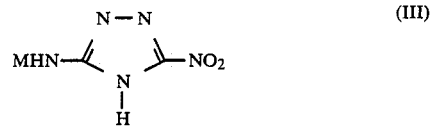

in which M represents a hydrogen atom or an alkali metal.

This process is based on a nucleophilic substitution reaction between 3-amino-5-nitro-1,2,4-triazole of formula 111 and a 4,6-di-halogeno-5-nitropyrimidine of formula 11, which are commercially available or easily synthesized starting reagents.

The reaction corresponds to the following reaction diagram:

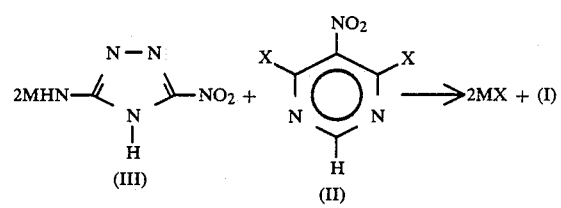

Preferably, use is made of the alkali metal salt of amino-5-nitro1,2,4-triazole. The alkali metal salt can be obtained by reacti 3-amino-5-nitro-1,2,4-triazole with an alkali metal alkoxide and in particular a lithium, sodium or potassium alkoxide, in accordance with the following reaction diagrams:

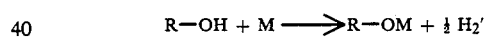

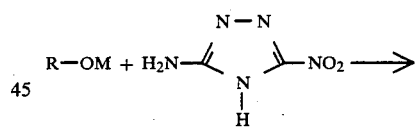

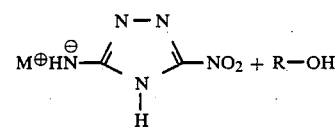

in which M is preferably Li, Na or K and R is an alkyl radical with 1 to 3 carbon atoms.

3-amino-5-nitro-1,2,4-triazole can be synthesized by conventional processes, e.g. by the nitration of 3-amino-1,2,4-triazole by a nitric acid-acetic anhydride mixture ($HNO_3$-$Ac_2O$).

3-amino-1,2,4-triazole is a commercial product used in the phytosanitary and photographic industries and is consequently readily available.

Prior to the effective nitration, the amine function of the 3-amino-1,2,4-triazole must be protected by acetylation:

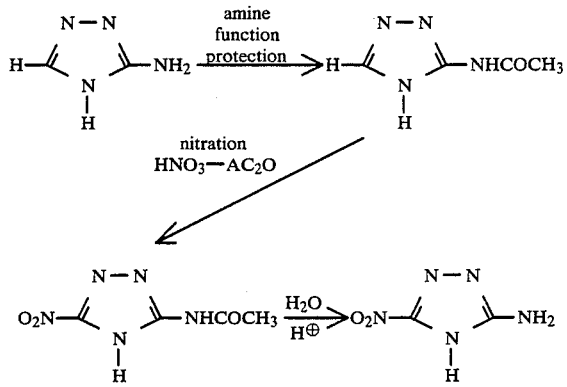

This synthesis is described by M.S. Pevzner et al in Khimiya Geterotsiklicheskikh Soedinenii, No. 8, pp.1132-35, 08/79.

The 4,6-dihalogeno-5-nitropyrimidine halide can be fluorine, chlorine or bromine. Preference is given in the inventive process to 4,6-dichloro-5-nitropyrimidine due to its good commercial availability and the high reactivity of its two chlorine atoms.

In order to carry out the reaction, synthesis firstly takes place of the alkali metal salt of 3-amino-5-nitro-1,2,4-triazole of formula III by placing same in an alkaline alkoxide solution, preferably sodium ethanolate. The alkali metal salt of formula III is obtained after refluxing for 30 minutes. The 4,6-dichloro-5-nitropyrimidine is then added in alcoholic solution, e.g. in absolute ethanol.

The reaction is obtained after refluxing for 3 hours and the final compound of formula I is freed from sodium chloride by successive washing operations in water under ultrasonics.

The pyrimidine derivative according to the invention can be used as the explosive material. In this case, said derivative is generally dispersed in a thermoplastic or thermosetting binder optionally containing other additives conventionally used in such compositions (plasticizers, dyes, etc.).

Other features and advantages of the invention can be better gathered from reading the following example obviously given in a non-limitative and illustrative manner.

This example illustrates the preparation of 4,6-di-(3-amino-5-nitro-1,2,4-triazole)-5-nitropyrimidine from commercially available 4,6-dichloro-5-nitropyrimidine and 3-amino-5-nitro-1,2,4-triazole, which is obtained from 3-amino-1,2,4-triazole.

1. Preparation of 3-amino-5-nitro-1,2,4-triazole, which firstly undergoes acetylation in order to protect the amine function and form the 3-acetamido-1,2,4-triazole derivative, which then undergoes nitration.

(a) Preparation of 3-acetamido-1,2,4-triazole.

1000 g of aminotriazole are progressively added to 3 liters of acetic anhydride preheated to 30° to 35° C. At the end of introduction, boiling takes place for 1 minutes. On returning to ambient temperature filtering and washing takes place with 1 liter of toluene. the precipitate is then dried and hydrolysed with 3 liters of water, followed by heating at 80° C. for 1 night. the 3-acetamido-1,2,4-triazole obtained is then filtered, washed with water and dried. The total yield is approximately 85 to 87%.

b) Preparation of 3-amino-5-nitro-1,2,4-triazole.

60 g of 3-acetamido-1,2,4-triazole obtained in a) are introduced progressively into a mixture of 224 ml of acetic anhydride and
100 ml of 100% nitric acid (d=1.52) cooled to −20° C. and said temperature is maintained for 30 minutes, followed by progressive heating to −5° C.

The solution is then precipitated on ice, filtered to eliminate the by-products and the filtrate is extracted with ethylene acetate. The organic phase is concentrated and 3-amino-5-nitro-1,2,4-triazole precipitates. The latter is filtered and then washed with ethyl ether. The total nitration yield is about 30%.

2. Preparation of 4,6-di-(3-amino-5-nitro-1,2,4-triazole)-5-nitropyrimidine.

To 100 ml of absolute ethanol are added in small fractions 0.92g of sodium, accompanied by stirring, until complete dissolving takes place. This is followed by the introduction of 5.16 of previously obtained aminonitrotriazole and refluxing takes place for 1 hour in order to prepare the alkali metal salt of formula IV. This is followed by the introduction of 3.88g of 4,6-dichloro-5-nitropyrimidine dissolved in approximately 60 ml of absolute ethanol and refluxing takes place for 3 hours. The product obtained is filtered and the NaCL formed eliminated by successive extractions in water under ultrasonics.

The total yield is 60%. The elementary analysis of the product obtained is as follows:

|  | C | H | N | O |
|---|---|---|---|---|
| Found | 25.43 | 1.35 | 47.80 | 25.35 |
| Calculated | 25.34 | 1.33 | 48.02 | 25.31 |

The product obtained appears in the form of a crystalline bright yellow solid, whose melting point is 310° C. (decomposition). Its density, measured with the gas pycnometer, is p=1.85. It is soluble in sulphuric acid and in very small proportions in N-methylpyrrolidene and dimethylsulphoxide (DMSO). It is insoluble in chlorinated solvents, aromatics, acetone, water, alcohols and di-methylformamide (DMF). Its specific surface is 2.14 m$^2$/g (measured by the BET method) and has the following properties:

I. Spectroscopic properties.

1) Nuclear magnetic resonance (NMR)

The following notations are adopted for the protons of the molecule:

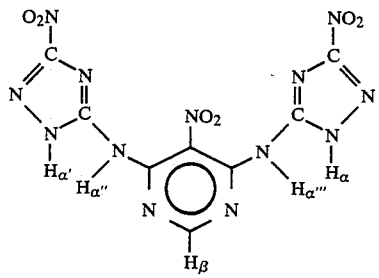

The limited solubility of the product only made it possible to obtain a ¹H proton spectrum at 60 MHz of the sample in solution in dimethyl sulphoxide (DMSOD$_6$). The latter has two peaks, namely one peak at 9.12 ppm due to the H proton ($\rho$) at 2 of the pyrimidine cycle and one peak at 8.70 ppm due to the H proton ($\alpha$) of the triazole cycle, as well as —NH between the triazole and pyrimidine cycles.

(2) Infrared spectrum

The infrared spectrum reveals a group of difficulty attributable bands indicating the presence of nitro aromatic cycles. There is also a wide mass between 2800 and 3600 cm$^{-1}$, the domain of $\nu$NH.

II. Thermal and detonation properties.

(1) Oxygen balance

The oxygen balance with respect to $CO_2$ and $H_2O$ is $-52.74$g of $O_2$ for 100g of product. For comparison, the oxygen balance of TATB is $-55.81$g/100g and that of octogen $-21.6$g/100g.

(2) Deflagration temperature

An approximately 20 mg sample in a stainless steel container is immersed in a bath whose temperature is raised 5° C./min. In the present case, the temperature at which the product deflagrates is 310° to 311° C.

(3) Thermal induction time

Approximately 10 mg of the product in a steel container are suddenly introduced into a bath at the measuring temperature and the time after which decomposition takes place is recorded. Considering that the kinetics are of order zero, it is possible to calculate the activation energy. Deflagration occurs after 5s at a temperature of 356° C. for 4,6-di-(3-amino-5-nitro-1,2,4-triazole)-5-nitropyrimidine. The activation energy of the reaction is 44.05 kcal/mole.

(4) Detonation velocity

The detonation velocity calculated on the basis of the empirical formula, in accordance with the empirical method of Rothstein and Petersen described in Propellants and Explosives, 4, 56–60, 1979 is 8600 m/s for the crystal density For comparison purposes and using the same method, the calculated detonation velocity of TATB is 7870 m/s and that of octogen is 9050 m/s.

(5) Shock sensitivity

The shock sensitivity of the product was determined with the aid of a 5 kg pendulum ram or weight, a sample of 30 mg being deposited on sandpaper. The test was performed in accordance with the Bruceton method.

Under such test conditions, the probability of 50% pyrotechnic reaction was obtained for a height of 61.5 cm. For comparison, the shock sensitivity of TATB corresponds to $H_{50} > 72$ cm and that of octogen to $H_{50} = 15$ cm.

Thus, 4,6-di-(3-amino-5-nitro-1,2,4-triazole)-5-nitropyrimidine has a low shock sensitivity, whilst being able to deliver a high energy.

We claim:
1. 4,6-di-(3-amino-5-nitro-1,2,4-triazole)-5-nitropyrimidine of formula:

* * * * *

UNITED STATES PATENT AND TRADEMARK OFFICE
CERTIFICATE OF CORRECTION

PATENT NO. : 4,970,311
DATED : November 13, 1990
INVENTOR(S) : Francois Laval et al.

It is certified that error appears in the above-identified patent and that said Letters Patent is hereby corrected as shown below:

Column 2, line 14, delete "lll" and insert --III--.

Column 2, line 15, delete "ll" and insert --II--.

Column 4, lines 9 and 10, delete "boiling takes place for 1 minutes" and insert --boiling takes place for 10 minutes--.

Column 5, line 25, delete "p" and insert --β--.

Please insert the following structural formula in Claim 1:

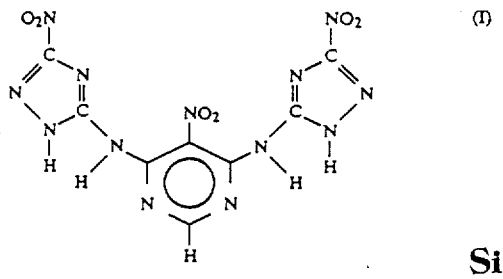

Signed and Sealed this

Nineteenth Day of May, 1992

Attest:

DOUGLAS B. COMER

*Attesting Officer*    *Acting Commissioner of Patents and Trademarks*